(12) United States Patent
Shah et al.

(10) Patent No.: US 7,771,744 B2
(45) Date of Patent: *Aug. 10, 2010

(54) BAZEDOXIFENE ACETATE FORMULATIONS

(75) Inventors: Syed M. Shah, East Hanover, NJ (US);
Christopher R. Diorio, Campbell Hall, NY (US); Eric C. Ehrnsperger, New City, NY (US); Kadum A. Ali, Congers, NY (US)

(73) Assignee: Wyeth LLC, Madison, NJ (US)

( * ) Notice: Subject to any disclaimer, the term of this patent is extended or adjusted under 35 U.S.C. 154(b) by 823 days.

This patent is subject to a terminal disclaimer.

(21) Appl. No.: 11/508,801

(22) Filed: Aug. 23, 2006

(65) Prior Publication Data
US 2007/0048374 A1    Mar. 1, 2007

Related U.S. Application Data

(60) Provisional application No. 60/710,761, filed on Aug. 24, 2005.

(51) Int. Cl.
| | |
|---|---|
| A61P 19/00 | (2006.01) |
| A61P 19/08 | (2006.01) |
| A61P 19/10 | (2006.01) |
| A61K 31/55 | (2006.01) |
| A61K 9/00 | (2006.01) |
| A61K 9/14 | (2006.01) |
| A61K 9/16 | (2006.01) |
| A61K 9/20 | (2006.01) |
| C07D 209/12 | (2006.01) |
| A61P 5/24 | (2006.01) |
| A61P 5/30 | (2006.01) |
| A61P 9/10 | (2006.01) |

(52) U.S. Cl. ............. 424/464; 514/217.08; 514/212.01; 540/602

(58) Field of Classification Search ................ None
See application file for complete search history.

(56) References Cited

U.S. PATENT DOCUMENTS

| | | | | |
|---|---|---|---|---|
| 5,686,094 | A | * | 11/1997 | Acharya ............... 424/434 |
| 5,998,402 | A | | 12/1999 | Miller et al. |
| 6,063,403 | A | * | 5/2000 | de Haan et al. ........ 424/464 |

(Continued)

FOREIGN PATENT DOCUMENTS

WO    WO-01/60816    8/2001

(Continued)

OTHER PUBLICATIONS

Miller et al., "Bazedoxifene Acetate," Drugs of the Future (2002) 27(2):117-121.*

Miller et al., "Design, synthesis, and preclinical characterization of novel, highly selective indole estrogens," *J Med Chem* (2001) 44:1654-1657.

(Continued)

*Primary Examiner*—Yvonne L Eyler
*Assistant Examiner*—Ivan Greene
(74) *Attorney, Agent, or Firm*—Ram W. Sabnis; Stephen E. Johnson

(57) ABSTRACT

Bazedoxifene acetate formulations and compositions thereof having improved properties relating to reduction, elimination, or prevention of polymorphic conversion of bazedoxifene acetate, and processes for making such formulations and compositions. Components used in the formulations and compositions include a filler/diluent, an optional second filler/diluent, an optional antioxidant, a glidant/disintegrant, and a lubricant.

47 Claims, 9 Drawing Sheets

U.S. PATENT DOCUMENTS

| | | |
|---|---|---|
| 6,479,535 B1 | 11/2002 | Pickar et al. |
| 2004/0063692 A1* | 4/2004 | Komm et al. .......... 514/217.09 |
| 2005/0227965 A1* | 10/2005 | Demerson et al. ...... 514/217.08 |
| 2005/0250762 A1 | 11/2005 | Ali et al. |

FOREIGN PATENT DOCUMENTS

| | | |
|---|---|---|
| WO | WO-02/03987 | 1/2002 |
| WO | WO-03/048133 | 6/2003 |
| WO | WO-2005/070434 | 8/2005 |
| WO | WO-2005/099677 | 10/2005 |
| WO | WO-2005/100314 | 10/2005 |
| WO | WO-2005/100316 | 10/2005 |

OTHER PUBLICATIONS

Miller et al., "Bazedoxifene Acetate," *Drugs of the Future* (2002) 27(2):117-121.

*Remington's Pharmaceutical Sciences*, 17$^{th}$ ed., Mack Publishing Company, Esaton, PA 1985.

International Search Report, issued May 9, 2007, for PCT/US2006/032935.

\* cited by examiner

BAZEDOXIFENE ACETATE FORMULATIONS

CROSS REFERENCE TO RELATED APPLICATIONS

This application claims priority benefit of U.S. Provisional Application Ser. No. 60/710,761, filed Aug. 24, 2005, the entire content of which is incorporated by reference in its entirety.

FIELD OF THE INVENTION

The present invention relates to formulations and compositions thereof of the selective estrogen receptor modulator 1-[4-(2-azepan-1-yl-ethoxy)-benzyl]-2-(4-hydroxy-phenyl)-3-methyl-1H-indol-5-ol acetic acid (bazedoxifene acetate).

BACKGROUND OF THE INVENTION

Bazedoxifene acetate(1-[4-(2-azepan-1-yl-ethoxy)-benzyl]-2-(4-hydroxy-phenyl)-3-methyl-1H-indol-5-ol acetic acid), having the chemical formula shown below:

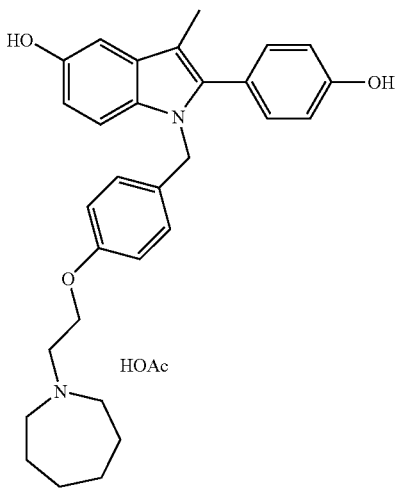

belongs to the class of drugs typically referred to as selective estrogen receptor modulators (SERMs). Consistent with its classification, bazedoxifene demonstrates affinity for estrogen receptors (ER) but shows tissue selective estrogenic effects. For example, bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene acetate is estrogenic on bone and cardiovascular lipid parameters and antiestrogenic on uterine and mammary tissue and thus has the potential for treating a number of different diseases or disease-like states wherein the estrogen receptor is involved.

U.S. Pat. Nos. 5,998,402 and 6,479,535 report the preparation of bazedoxifene acetate and characterize the salt as having a melting point of 174-178° C. The synthetic preparation of bazedoxifene acetate has also appeared in the general literature. See, for example, Miller et al., *Drugs of the Future,* 2002, 27(2), 117-121, which reports the salt as a crystalline solid having a melting point of 170.5-172.5° C. Further description of the drug's biological activity has appeared in the general literature as well (e.g. Miller, et al. *Drugs of the Future,* 2002, 27(2), 117-121; Miller et al., *J. Med. Chem.,* 2001, 44, 1654-1657).

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to make both polymorphs in pure form. In deciding which polymorph is preferable, the numerous properties of the polymorphs must be compared and the preferred polymorph chosen based on the many physical property variables. It is entirely possible that one polymorph form can be preferable in some circumstances where certain aspects such as ease of preparation, stability, etc are deemed to be critical. In other situations, a different polymorph maybe preferred for greater solubility and/or superior pharmacokinetics.

Because of the potential advantages associated with one pure polymorphic form, it is desirable to prevent or minimize polymorphic conversion (i.e., conversion of one form to another) when two or more polymorphic forms of one substance can exist. Such polymorph conversion can occur during both the preparation of formulations containing the polymorph, and during storage of a pharmaceutical dosage form containing the polymorph. Two different crystalline polymorphs of anhydrous bazedoxifene acetate, form A and form B, have been disclosed in U.S. patent application Ser. Nos. 11/100,983 and 11/100,998, both filed Apr. 6, 2005 and each of which is incorporated by reference herein in its entirety. Form A is distinguished from Form B by numerous physical properties which are tabulated below. As can be seen from the data in the Table, Form B appears to be thermodynamically more stable than form A, contributing to numerous advantages. For example, the increased stability of form B would facilitate manufacturing and purification processes. Form B would also be expected to have better resistance to degradation brought on by, for example, exposure to high temperatures and/or humidity, and have a longer shelf-life than Form A or amorphous material. In contrast, Form A appears to have higher solubility in aqueous and organic solvent systems than does form B, which is advantageous in particular formulations or doses where the solubility of the particular composition is of concern. For example, higher solubility can contribute to better biological absorption and distribution of the drug, as well as facilitate formulation in liquid carriers.

TABLE

| Measurement | Form A | Form B |
| --- | --- | --- |
| Melting Point | 176° C. | 181° C. |
| Heat of Fusion | 94.6 J/G | 108.4 J/G |
| Solubility-Water | 0.49 mg/mL | 0.23 mg/mL |
| Solubility-Org (EtOH/EtOAc/Tol) | 24.5 mg/mL | 12.4 mg/mL |
| Intrinsic Dissolution Rate | 0.125 mg/cm$^2$-min | 0.09 mg/cm$^2$-min |
| DSC | Single Melting Endotherm 176.1° C. | Single Melting Endotherm 181.1° C. |
| TGA | Similar | Similar |
| X-Ray Powder | 12.7°, 16.0°, 18.5°, 20.7°, 22.3° (2θ) | 13.3°, 20.8°, 21.6°, 25.0° (2θ) |
| Raman/IR | 1511, 1467 cm$^{-1}$ | 1513, 1449, 1406 cm$^{-1}$ |

Given the potential advantages of a single polymorphic form, it can be seen that formulations having reduced polymorphic conversion can provides significant benefits. The bazedoxifene acetate formulations and compositions described herein helps meet these and other needs.

SUMMARY OF THE INVENTION

In some embodiments, the present invention provides pharmaceutical compositions, for example tablets, comprising bazedoxifene acetate and a pharmaceutically acceptable carrier or excipient system. In some embodiments, the carrier or excipient system includes:

a) a first filler/diluent component comprising from about 5% to about 85% by weight of the pharmaceutical formulation;

b) an optional second filler/diluent component comprising from about 5% to about 85% by weight of the pharmaceutical formulation;

c) an optional antioxidant component comprising up to about 15% by weight of the pharmaceutical formulation;

d) a glidant/disintegrant component comprising from about 0.01% to about 10% by weight of the pharmaceutical formulation; and e) a lubricant component comprising from about 0.01% to about 10% by weight of the pharmaceutical formulation.

In some embodiments, the compositions are prepared by a non-aqueous process, for example dry granulation, roller compaction, or direct blend processes.

In some embodiments, the compositions of the invention are tablets, prepared by a direct blending procedure.

In some embodiments, the bazedoxifene acetate comprises from about 0.1% to about 30% by weight of the pharmaceutical formulation; or from about 10% to about 30% by weight of the pharmaceutical formulation.

In some embodiments, the bazedoxifene acetate is present substantially in a crystalline polymorphic form; preferably substantially in the A polymorph form. In further embodiments, at least about 90% of the bazedoxifene acetate is present in the A polymorph form. In some further embodiments, at least about 80% of said bazedoxifene acetate is present in the A polymorph form.

In further embodiments, the invention provides processes for making the compositions of the invention, and products of the processes.

DETAILED DESCRIPTION

Figure 1:
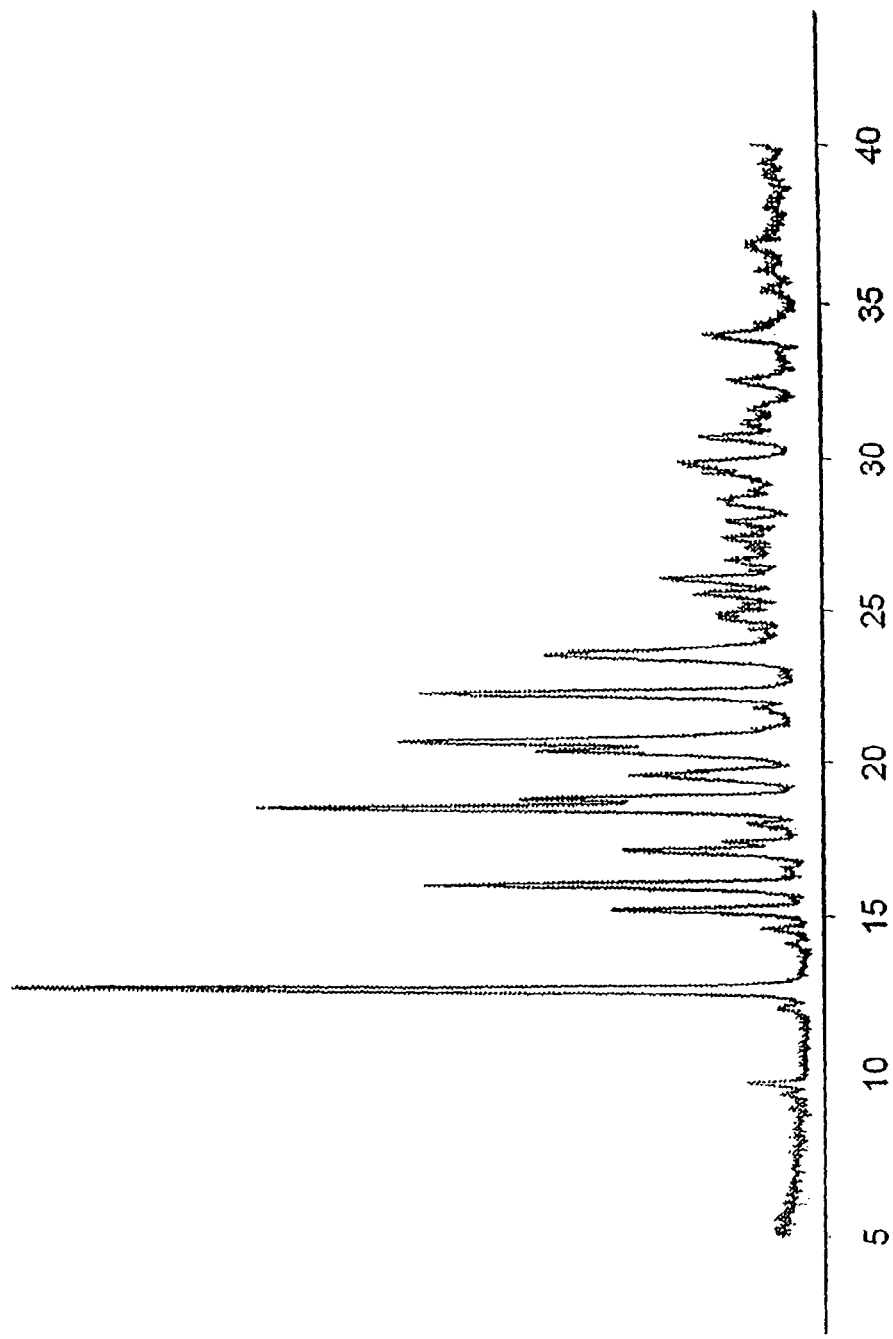
FIG. 1 depicts a powder X-ray diffraction pattern of bazedoxifene acetate Form A polymorph.

The present invention provides, inter alia, bazedoxifene acetate formulations and compositions thereof having improved properties relating to reduction, elimination or prevention of polymorphic conversion of bazedoxifene acetate. In some embodiments, the compositions are prepared by a non-aqueous process, for example dry granulation, roller compaction or direct blend processes. In some embodiments, the present invention provides a direct blend formulation of bazedoxifene acetate that can reduce the potential for polymorphic conversion of bazedoxifene acetate, such as from form A to form B, compared to other more complex formulations.

The use of a direct blend formulation is simple and cost-efficient compared to other more time consuming processes such as wet granulation or roller-compaction, although roller compaction processes can be utilized in some embodiments of the invention. Many of the complex formulations such as roller compaction require large power inputs during mixing, milling and compaction. In addition, a process with power input for an extended period of time can also increase potential polymorphic conversions. Thus, another advantage associated with a direct blend formulation is to use lower power in the process.

While not wishing to be bound by any particular theory, it is believed the use of water in a wet granulation has the potential of increasing polymorphic conversion during processing and storage because of the potential for solubilization of the bazedoxifene acetate. Upon drying, recrystallization of the bazedoxifene acetate can result in polymorphic conversion, such as from form A to form B. Accordingly, in one aspect, the present invention provides non-aqueous processes (i.e. processes that do not utilize water) for producing the pharmaceutical compositions described herein. Examples of such non-aqueous processes include dry granulation and roller compaction processes, as are known in the art. In one particular embodiment, the non-aqueous process is a direct blend process, which is used to prepare direct blend formulations of bazedoxifene acetate, and which does not require contacting the bazedoxifene acetate with water. Such non-aqueous processes can be advantageous where it is desired to minimize conversion from one polymorphic form of bazedoxifene acetate to another, for example to minimize the conversion of the form A polymorph to the form B polymorph.

A further advantage of the present compositions is that there is no need to employ a surfactant, such as sodium lauryl sulfate. While not wishing to be bound by any particular theory, it is believed the use of a surfactant can increase wetting, solubility and dissolution, and the increased solubility can facilitate potential polymorphic conversion between the different polymorphic forms.

In some embodiments, the present invention provides pharmaceutical compositions comprising a pharmaceutically effective amount of bazedoxifene acetate, and a carrier or excipient system, the carrier or excipient system comprising:

A pharmaceutical composition comprising a pharmaceutically effective amount of bazedoxifene acetate and a carrier or excipient system, the carrier or excipient system comprising:

a) a first filler/diluent component comprising from about 5% to about 85% by weight of the pharmaceutical formulation;

b) an optional second filler/diluent component comprising from about 5% to about 85% by weight of the pharmaceutical formulation;

c) an optional antioxidant component comprising up to about 15% by weight of the pharmaceutical formulation;

d) a glidant/disintegrant component comprising from about 0.01% to about 10% by weight of the pharmaceutical formulation; and e) a lubricant component comprising from about 0.01% to about 10% by weight of the pharmaceutical formulation. In some embodiments, the compositions are prepared by a non-aqueous process, for example a dry granulation, roller compaction or direct blend process.

In some embodiments, the compositions of the invention contain bazedoxifene acetate substantially in one pure crystalline polymorph, preferably substantially in the A polymorph form. In further embodiments, at least about 90% of the bazedoxifene acetate is present in the A polymorph form. In some further embodiments, at least about 80% of said bazedoxifene acetate is present in the A polymorph form. The direct blend formulations of the present invention have improved properties relating to reduction, elimination or prevention of polymorphic conversion of bazedoxifene acetate, such as from form A to form B, during preparation of the compositions, and during storage thereafter. Therefore, the formulations of the present invention more effectively maintain advantages associated with a single polymorph form.

Those of skill in the art will be able to readily ascertain pharmaceutically effective amounts of bazedoxifene acetate. Generally, on a percentage basis, the bazedoxifene acetate is present in an amount of from about 0.1% to about 30% by weight of the pharmaceutical compositions of the present invention. In some embodiments, the bazedoxifene acetate is present in an amount of from about 10% to about 30% by weight of the composition. In some embodiments, the bazedoxifene acetate is present in an amount of from about 10% to about 25% by weight of the composition.

As will be appreciated, the compositions of the invention can be prepared as, or incorporated into, a variety of dosage forms, for example tablets and capsules. In some embodiments, the invention provides tablets that contain, or are composed of a composition of the invention. Generally, tablet dosage forms of the invention can contain bazedoxifene acetate in an amount of from about 0.1 mg to about 300 mg. In further embodiments, the dosage forms can include bazedoxifene acetate in an amount of from about 0.5 to about 230 mg, from about 1 to about 170 mg, from about 5 to about 115 mg, or from about 1 to about 30 mg. In some embodiments, the invention provides dosage forms, for example tablets, containing a composition of the invention that includes bazedoxifene acetate in an amount of from about 15 mg to about 25 mg.

Generally, the first filler/diluent component, and the optional second filler/diluent component, when present, can be present in an amount of from about 5% to about 85% by weight of the pharmaceutical formulation, or from about 25% to about 50% by weight of the pharmaceutical formulation. In one embodiment the first filler/diluent component, and the optional second filler/diluent component are present in an amount of from about 25% to about 40% or more, e.g. to about 42%, by weight of the pharmaceutical formulation.

Both the first filler/diluent component and the optional second filler/diluent component can be selected from fillers and diluents known to be useful in the art, including for example one or more of sugars, for example sucrose, mannitol, lactose, and the like, and/or other fillers such as powdered cellulose, malodextrin, sorbitol, xylitol, carboxymethyl cellulose, carboxyethyl cellulose, hydroxyethyl celluloses, microcrystalline celluloses, starches, calcium phosphates, for example anhydrous dicalcium phosphate, sodium starch glycolates, metal aluminosilicates, for example magnesium aluminometasilicate (Neusilin), and a mixture thereof. In some embodiments, the first filler/diluent component includes or consists of microcrystalline cellulose, for example AVICEL PH101® (microcrystalline cellulose), and the second filler/diluent includes or consists of lactose, for example lactose NF.

As used herein, the term "sugar" refers to any type of simple carbohydrate, such as a mono or disaccharide, either naturally obtained, refined from a natural source, or artificially produced, and includes, without limitation, sucrose, dextrose, maltose, glucose, fructose, galactose, mannose, lactose, trehalose, lactulose, levulose, raffinose, ribose, and xylose. The term "sugar," as used herein, also includes various "sugar substitutes" widely known to those of ordinary skill in the art of preparing solid dosage forms, such as the polyhydric alcohols (sometimes referred to as "sugar alcohols" or hydrogenated saccharides), for example sorbitol, mannitol, xylitol, and erythritol, and the sugar derivatives of polyhydric alcohols, such as maltitol, lactitol, isomalt, and polyalditol. Accordingly, the recitation of the term "sugar" generically should be interpreted to include such specific compounds, as well as others not expressly recited. In certain embodiments, the sugar is a mono- or disaccharide, for example, sucrose, dextrose, maltose, glucose, fructose, galactose, mannose, or lactose. In some embodiments, the second filler/diluent component of the compositions of the invention include or consist of lactose.

Generally, the glidant/disintegrant component is present in an amount of from about 0.01% to about 10% by weight of the pharmaceutical formulation, or from about 1% to about 10% by weight of the pharmaceutical formulation, or from about 3% to about 5% by weight of the pharmaceutical formulation. The glidant/disintegrant can be selected from glidants and disintegrants know to be useful for pharmaceutical formulations. Examples of suitable glidant/disintegrants include croscarmellose sodium, modified cellulose, pregelatinized starch, sodium starch glycolate, crospovidone, starch, alginic acid, sodium alginate, clays, cellulose floc, ion exchange resins, effervescent systems based on food acids, AEROSIL 200® (amorphous fumed silica), talc, lactose, stearates, dibasic calcium phosphate, magnesium carbonate, magnesium oxide, calcium silicate, silica, silicon dioxide, silicon dioxide aerogels and mixtures thereof. In some embodiments, the glidant/diluent includes or consists of sodium starch glycolate.

The lubricant component is generally present in an amount of from about 0.01% to about 10% by weight of the pharmaceutical formulation, from about 0.01% to about 3% by weight of the pharmaceutical formulation, or from about 0.01% to about 2% by weight of the pharmaceutical formulation. In some embodiments, the lubricant component is present in an amount of about 1% by weight of the pharmaceutical formulation. The lubricant component can be selected from the many lubricants useful in the pharmaceutical arts. Examples of suitable lubricants include metal stearates, fatty acid esters, fatty acids, fatty alcohols, glyceryl behenate, mineral oil, paraffins, hydrogenated vegetable oils, leucine, polyethylene glycols, AEROSIL 200® (amorphous fumed silica), sodium chloride and mixtures thereof. In some preferred embodiments, the lubricant is a metal stearate, for example, magnesium stearate.

In some embodiments, the pharmaceutical formulations and excipient systems of the invention also contain an antioxidant component, which can be a single compound, such as ascorbic acid, or a mixture of antioxidants. A wide variety of antioxidant compound are known in the art, and are suitable for use in the present invention. Examples of such antioxidants that can be used in the present invention include sodium ascorbate, ascorbyl palmitate, BHT (butylated hydroxytoluene) and BHA (butylated hydroxyanisole), each optionally in conjunction with an amount of ascorbic acid. Generally, the antioxidant component, when present, is used in an amount of up to about 15% by weight of the pharmaceutical formulation, for example from about 1% to about 10% by weight of the pharmaceutical formulation, or from about 2% to about 8% by weight of the pharmaceutical formulation.

Additional suitable filler/diluents, antioxidants, glidant/disintegrants and lubricants can be found in, for example, Remington's Pharmaceutical Sciences, 17th ed., Mack Publishing Company, Easton, Pa., 1985, which is incorporated herein by reference in its entirety.

In some embodiments, the first filler/diluent component includes one or more of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, anhydrous dicalcium phosphate, sodium starch glycolates, or metal aluminosilicates; the optional second filler/diluent component includes one or more of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, anhydrous dicalcium phosphate, sodium starch glycolates, or metal aluminosilicates; the optional antioxidant component, when present, includes one or more of ascorbic acid, sodium ascorbate or ascorbyl palmitate; the glidant/disintegrant component includes one or more of croscarmellose sodium, modified cellulose, pregelatinized starch, sodium starch glycolate, crospovidone, starch, alginic acid, sodium alginate, clays, cellulose floc, ion exchange resins, effervescent systems based on food acids, AEROSIL 200® (amorphous fumed silica), talc, lactose, metal stearates, dibasic calcium phosphate, magnesium carbonate, magnesium oxide, calcium silicate, silica, silicon dioxide and silicon dioxide aerogels; and the lubricant component includes one or more of metal stearates, fatty acid esters, fatty acids, fatty alcohols, glyceryl behenate, mineral oil, paraffins, hydrogenated vegetable oils, leucine, polyethylene glycols, AEROSIL 200® (amorphous fumed silica), and sodium chloride.

In some preferred embodiments, the first filler/diluent component includes or consists of microcrystalline cellulose, for example AVICEL PH101® (microcrystalline cellulose); the optional second filler/diluent component is present, and includes or consists of a sugar, for example lactose NF; the optional antioxidant component is present, and includes or consists of ascorbic acid; the glidant/disintegrant component includes or consists of sodium starch glycolate; and the lubricant component includes or consists of a metal stearate, for example magnesium stearate.

In some embodiments, the invention further provides non-aqueous processes for preparing a pharmaceutical composition comprising a pharmaceutically effective amount of bazedoxifene acetate and a carrier or excipient system, the carrier or excipient system comprising:

a) a first filler/diluent component comprising from about 5% to about 85% by weight of the pharmaceutical formulation;

b) an optional second filler/diluent component comprising from about 5% to about 85% by weight of the pharmaceutical formulation;

c) an optional antioxidant component comprising up to about 15% by weight of the pharmaceutical formulation;

d) a glidant/disintegrant component comprising from about 0.01% to about 10% by weight of the pharmaceutical formulation; and e) a lubricant component comprising from about 0.01% to about 10% by weight of the pharmaceutical formulation. Examples of suitable non-aqueous processes include direct blending, dry granulation and roller compaction.

In some embodiments, the non-aqueous process is a direct blend process. In some such embodiments, the process comprises:

i) combining the bazedoxifene acetate, first filler/diluent, second filler/diluent, glidant, and, optionally, the antioxidant to form a first mixture;

ii) blending the first mixture to form a blended first mixture;

iii) adding the lubricant to the blended first mixture to form a second mixture; and iv) optionally blending the second mixture to form a blended second mixture; and v) optionally,
compressing at least a portion of said second mixture, or said blended second mixture, to form a tablet therefrom; or
filling a capsule with said second mixture, or said blended second mixture, to provide a capsule filled with said second mixture, or said blended second mixture.

Generally, it is preferred that the bazedoxifene acetate is micronised prior to combination with the other components of the formulation.

The order of addition of the components (i.e., the bazedoxifene acetate, first and second filler/diluents, antioxidant, lubricant and glidant) is not critical, although it is generally preferred that the bazedoxifene acetate, first and second filler/diluents, antioxidant and glidant be combined and blended prior to blending with the lubricant.

The tablets can further include one or more surface coatings, for example clear coatings and/or color coatings. Numerous coatings and procedures for their application are known in the art, including those disclosed in Remington's Pharmaceutical Sciences, supra.

The processes of the invention are useful, inter alia, to provide compositions of the invention, and dosage forms containing the compositions, that include a preponderance of one polymorphic form of bazedoxifene acetate. In some embodiments, the bazedoxifene acetate is present substantially in a crystalline polymorphic form. In some embodiments, the bazedoxifene acetate is present substantially in form A polymorph; i.e., there is no detectable B polymorph present, as determined by Raman spectroscopy or X-ray diffraction. In some embodiments, at least about 90% of the bazedoxifene acetate is present in the A polymorph form. In further embodiments, at least about 80% of the bazedoxifene acetate is present in the A polymorph form. The determination of the amount of the A or B polymorphic form can be accomplished by, for example, Raman spectroscopy or X-ray diffraction.

The present invention also provides products of the processes described herein.

It will be understood that the weight percentages set forth for the bazedoxifene acetate, first filler/diluent component, the optional second filler component, antioxidant component, glidant/disintegrant component, and lubricant component of the compositions disclosed herein are the percentages that each component will comprise of a final pharmaceutical composition, without reference to any surface covering, such as a tablet coating (for example any clear or color coating) or capsule.

Oral formulations containing the present solid dispersions can comprise any conventionally used oral forms, including tablets, capsules, buccal forms, troches, lozenges, suspensions, and the like. In some embodiments, the dosage form is a tablet. Capsules or tablets of containing the present solid dispersion can also be combined with mixtures of other active compounds or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. In some preferred embodiments, the formulations are direct blend solid dispersions compressed into tablets.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations used herein may utilize standard delay or time release formulations or spansules. Suppository formulations may be made from traditional materials, including cocoa butter, with or without the addition of waxes to alter the suppositories melting point, and glycerin. Water soluble suppository bases, such as polyethylene glycols of various molecular weights, may also be used.

In some embodiments, the dosage forms of the invention are direct blend tablets. Such tablets can generally range from about 50 mg to about 1000 mg, depending upon the dosage required for therapeutic use. In some embodiments, the dosage forms are 200 mg tablets, containing a sufficient amount of bazedoxifene acetate to provide 20 mg of bazedoxifene, based on the weight of the free acid. In some further embodiments, the compositions and dosage forms of the invention include a sufficient amount of bazedoxifene acetate to provide 10 mg, 20 mg, 50 mg, 75 mg, 100 mg, 120 mg, 125 mg, 150 mg, 175 mg, 200 mg, 225 mg or 250 mg of bazedoxifene, based on the weight of the free acid.

Film coatings useful with the present formulations are known in the art and generally consist of a polymer (usually a cellulosic type of polymer), a colorant and a plasticizer. Additional ingredients such as sugars, flavors, oils and lubricants can be included in film coating formulations to impart certain characteristics to the film coat. The compositions and formulations herein may also be combined and processed as a solid, then placed in a capsule form, such as a gelatin capsule.

As will be appreciated, some components of the formulations of the invention can possess multiple functions. For example, a given component can act as both a diluent and a disintegrant. In some such cases, the function of a given component can be considered singular, even though its properties may allow multiple functionality.

Additional numerous various excipients, dosage forms, dispersing agents and the like that are suitable for use in connection with the solid dispersions of the invention are known in the art and described in, for example, *Remington's Pharmaceutical Sciences*, 17th ed., Mack Publishing Company, Easton, Pa., 1985, which is incorporated herein by reference in its entirety.

The materials, methods, and examples presented herein are intended to be illustrative, and are not intended to limit the scope of the invention. All publications, patent applications, patents, and other references mentioned herein are incorporated by reference in their entirety.

EXAMPLE 1

Procedure for Preparation of 100 mg Tablets Containing 20 mg of Bazedoxifene (as Acetate)

A. Bazedoxifene acetate (2,256 g), AVICEL PH101® (microcrystalline cellulose) (3,276 g), lactose NF (fast flow; 3,276 g), ascorbic acid (680 g) and sodium starch glycolate (412 g) are combined in a tumble blender and blended to form a mixture;

B. magnesium stearate (100 g) is added to the blended first mixture to form a second mixture, which is then blended again;

C. the blended mixture is then compressed to form tablets having final weight of 100 mg.

The composition of the tablets is shown in the Table below.

| Ingredient | % WT/WT | mg/tablet |
|---|---|---|
| AVICEL PH101 ® (microcrystalline cellulose) | 32.76 | 32.76 |
| Lactose, NF (fast flow) | 32.76 | 32.76 |
| Ascorbic Acid, USP | 6.80 | 6.80 |
| Sodium Starch Glycolate | 4.12 | 4.12 |
| Magnesium Stearate | 1.00 | 1.00 |
| Bazedoxifene acetate (88.68% bazedoxifene free base)[a,b] | 22.56 | 22.56 |
| TOTAL | 100.00 | 100 mg |

[a]The potency of bazedoxifene acetate may vary, and the amount in the formula must be adjusted accordingly with a corresponding adjustment in the amount of AVICEL PH101 ® (microcrystalline cellulose).
[b]22.56 mg of bazedoxifene acetate provides 20 mg of bazedoxifene.

EXAMPLE 2

Procedure for Preparation of 200 mg Tablets Containing 20 mg of Bazedoxifene (as Acetate)

The procedure is similar to that of Example 1, except that the amounts of the components used are: bazedoxifene acetate (1,128 g), AVICEL PH101® (microcrystalline cellulose) (4,036 g), lactose NF (fast flow; 4,036 g), ascorbic acid (300 g), sodium starch glycolate (400 g) and magnesium stearate (100 g).

The composition of the tablets is shown in the Table below.

| Ingredient | % WT/WT | mg/tablet |
|---|---|---|
| AVICEL PH101 ® (microcrystalline cellulose) | 40.36 | 80.72 |
| Lactose, NF (fast flow) | 40.36 | 80.72 |
| Ascorbic Acid, USP | 3.00 | 6.00 |
| Sodium Starch Glycolate | 4.00 | 8.00 |

-continued

| Ingredient | % WT/WT | mg/tablet |
|---|---|---|
| Magnesium Stearate | 1.00 | 2.00 |
| Bazedoxifene acetate (88.68% bazedoxifene free base)[a,b] | 11.28 | 22.56 |
| TOTAL | 100.00 | 200 mg |

[a]The potency of bazedoxifene acetate may vary, and the amount in the formula must be adjusted accordingly with a corresponding adjustment in the amount of AVICEL PH101 ® (microcrystalline cellulose).
[b]22.56 mg of bazedoxifene acetate provides 20 mg of bazedoxifene.

EXAMPLE 3

Procedure for Preparation of Form A

A 2 gal hydrogenation vessel with agitator was charged with hexamethyleneimino benzyloxyindole (250 g, 0.3841 mol; see U.S. Pat. No. 5,998,402 for a preparation), ethanol (denatured with 5% by volume ethyl acetate) (1578 g, 2000 mL), and palladium on carbon 10% (25 g). The reactants were hydrogenated at 25° C. and 50 psi for 20 hours. Reaction progress was monitored by HPLC (Column: CSC-S ODS 2, 25 cm; Mobile phase: 20% 0.02 M $NH_4H_2PO_4$ (2 mL TEA/L, pH=3) and 80% MeCN; Flow: 2 mL/min; Detector: 220 nm). The reaction was considered complete when less than 1% of either the hexamethyleneimino benzyloxyindole (18.2 min retention time) or mono-debenzylated derivative thereof (5.1 min retention time) was detected.

The mixture was filtered through a cartridge which was subsequently rinsed with ethanol (denatured with 5% by volume ethyl acetate) (2×198 g, 2×250 mL). The filtrate was transferred to a 5 L multi-neck flask with agitator charged with L-ascorbic acid (2.04 g, 0.0116 mols) under nitrogen. Acetic acid (34.6 g, 0.5762 moles) was added at 20° C. while stirring. The resulting reaction mixture was stirred for 2 hours (pH was about 5 and crystallization began within about 10 minutes of addition of acetic acid). The reaction mixture was then cooled to 0° C. and maintained at this temperature for 2 hours. The resulting solid was collected by filtration on a Buchner funnel and washed with ethanol (denatured with 5% by volume ethyl acetate) (2×150 g, 2×190 mL) at 0° C.

The solid product was further purified by charging a 3 L multineck flask (with agitator, thermometer, and condenser under nitrogen) with the filtered solid, ethanol (denatured with 5% by volume ethyl acetate) (1105 g, 1400 mL), and L-ascorbic acid (1.73 g, 0.01 mols). The resulting mixture was heated to 75° C. and cooled to 20° C. over the course of 2 hours. The resulting suspension was further cooled to 0° C. and held at this temperature for 2 hours. The resulting solid product was collected by filtration with a Buchner funnel and washed with ethanol (denatured with 5% by volume ethyl acetate) (2×79 g, 2×100 mL) at 0° C. The product was dried in vacuo at 60° C., 5 mm Hg for 24 hours giving 151.3 g bazedoxifene acetate Form A (74.2% yield).

EXAMPLE 4

Characterization of Form A

X-Ray Powder Diffraction (XRPD)

XRPD analyses were carried out on a (Scintag X2) X-ray powder diffractometer using Cu Kα radiation. The instrument was equipped with tube power, and amperage was set at 45 kV and 40 mA. The divergence and scattering slits were set at 1° and the receiving slit was set at 0.2 mm. A theta-two theta continuous scan at 3°/min (0.4 sec/0.02° step) from 3 to 40°2θ was used.

XRPD data are provided in the Table below. The corresponding XRPD pattern is provided in FIG. 1.

| XRPD Data for Form A | |
|---|---|
| Degree (2θ) | Intensity, Counts Per Second (CPS) |
| 9.8 | 180 |
| 12.7 | 3111 |
| 15.2 | 683 |
| 16.0 | 1347 |
| 17.1 | 591 |
| 17.4 | 220 |
| 18.5 | 1964 |
| 18.8 | 970 |
| 19.6 | 482 |
| 20.4 | 894 |
| 20.7 | 1440 |
| 22.3 | 1373 |
| 23.5 | 822 |
| 24.9 | 145 |
| 25.6 | 231 |
| 26.1 | 346 |
| 27.4 | 147 |
| 28.0 | 152 |
| 28.7 | 153 |
| 29.6 | 202 |
| 29.9 | 307 |
| 30.7 | 268 |

Infrared (IR) Spectroscopy

IR spectra (e.g., see FIG. 2) were acquired as follows. Samples were prepared as potassium bromide (KBr) discs (or pellets). A small amount of each sample (about 3 mg) was ground in a hard surface mortar until glossy in appearance. One half gram (0.5 g) of KBr was added to the sample and the mixture was continuously ground until well mixed. The mixture was then transferred to a die and pressed into a disc using a hydraulic press.

Figure 2:
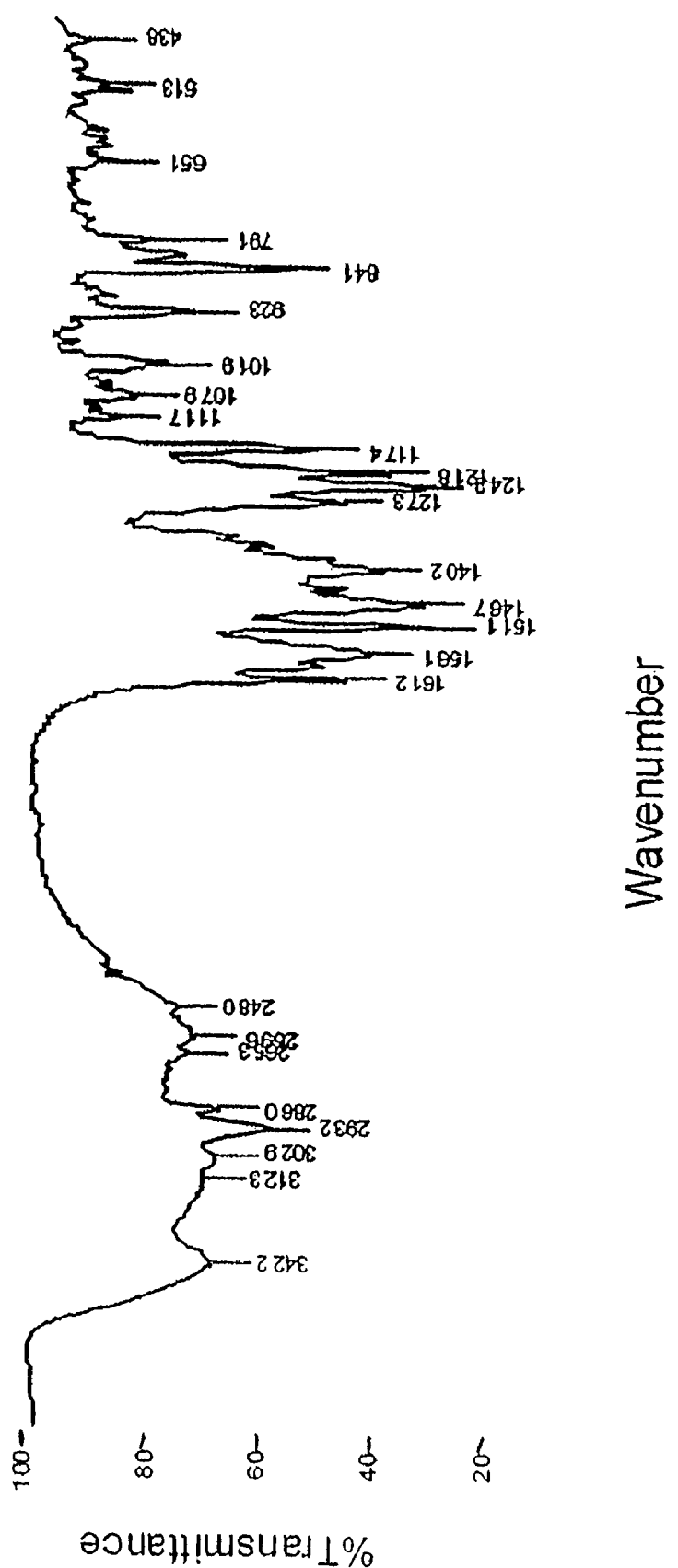
FIG. 2 depicts an IR spectrum of bazedoxifene acetate Form A polymorph in KBr pellet.

The IR spectrum of FIG. 2 was obtained using a DIGILAB EXCALIBUR Series FTS-4000 FT-IR Spectrometer operated at 4 $cm^{-1}$ resolution and 16 scans between 400-4000 $cm^{-1}$.

Differential Scanning Calorimetry (DSC)

Figure 3:
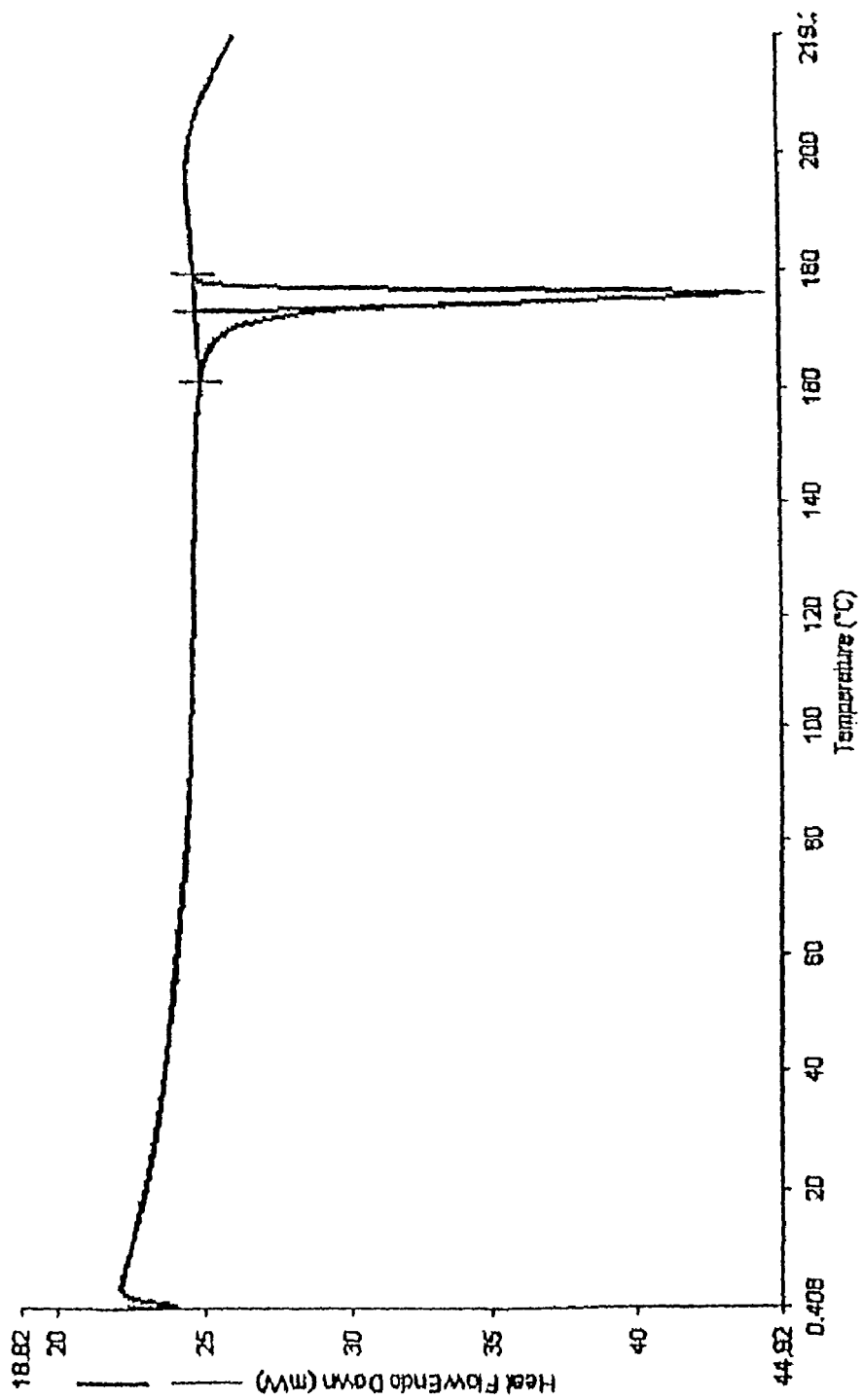
FIG. 3 depicts a differential scanning calorimetric (DSC) trace of bazedoxifene acetate Form A polymorph.

DSC measurements (see FIG. 3) were carried out in both sealed pan and vented pan at a scan rate of 10° C./min from 25° C. to 200° C. under nitrogen purge using a Pyris I DSC from Perkin-Elmer.

EXAMPLE 5

Procedure for Preparation of Form B

Preparation of Bazedoxifene Acetate Form B from Form A

To a stirred solution of 594 g of ethanol (denatured with 5% of acetone and with 3% of cyclohexane) and 184 g of ethyl acetate, 400 g of pure bazedoxifene acetate Form A were added under nitrogen (e.g., see Example 2). The heterogeneous mixture was kept at 30° C. and stirred overnight under nitrogen.

The completion of the crystalline transformation was determined by DSC analysis. The mixture was cooled to 0° C. and stirred for 2 hrs under nitrogen. The product was filtered, washed with a mixture of denatured ethanol and ethyl acetate as above and dried overnight at 60° C. under vacuum giving 391 g (97.7% yield) of bazedoxifene acetate Form B polymorph.

A substantially identical result was obtained using absolute ethanol or ethanol denatured with 5% toluene.

Preparation of Bazedoxifene Acetate Form B from a Mixture of Form A and Form B

Bazedoxifene acetate Form A (298 g) and bazedoxifene acetate Form B (2 g) were suspended in a degassed mixture of ethyl acetate (400 mL) and ethyl alcohol (2400 mL). The resulting mixture was heated at reflux temperature for 2 hours. The suspension was cooled to 50° C. over the course of 1 hour and then to 20° C. over the course of 3 hours. The mixture was maintained at 20° C. for 13 hours and the product was recovered by filtration and washing with ethyl alcohol (78.9 g divided in 2 portions). The wet material was dried under vacuum at 60° C. resulting in 276.8 g of bazedoxifene acetate Form B.

EXAMPLE 6

Characterization of Form B

X-Ray Powder Diffraction (XRPD)

XRPD analyses were carried out on a (Scintag X2) X-ray powder diffractometer using Cu Kα radiation. The instrument was equipped with tube power, and amperage was set at 45 kV and 40 mA. The divergence and scattering slits were set at 1° and the receiving slit was set at 0.2 mm. A theta-two theta continuous scan at 3°/min (0.4 sec/0.02° step) from 3 to 40°2θ was used.

Figure 4:
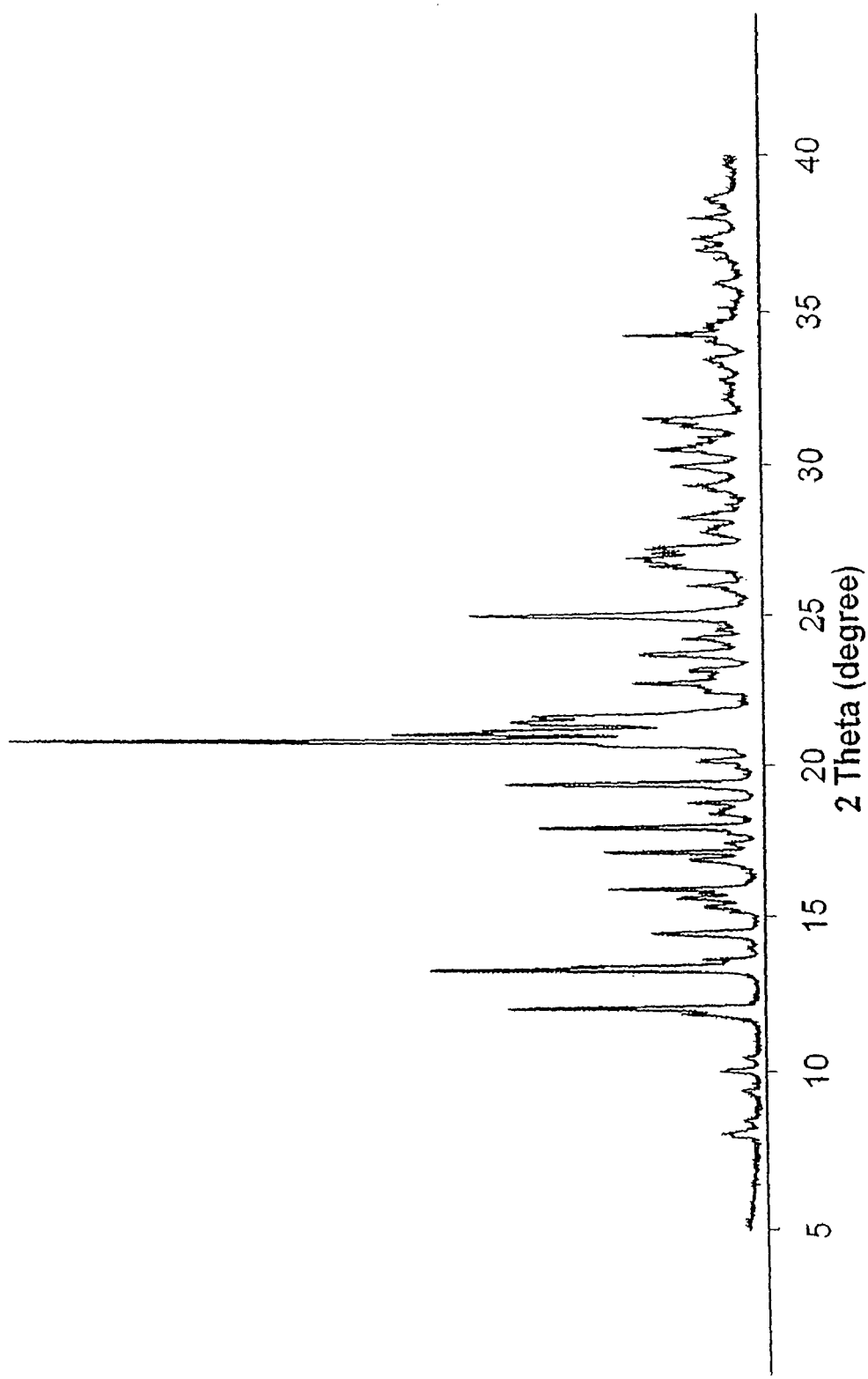
FIG. 4 depicts a powder X-ray diffraction pattern of the bazedoxifene acetate Form B polymorph.

XRPD data are provided in the Table below. The corresponding XRPD pattern is provided in FIG. 4.

XRPD Data for Form B

| Degree (2θ) | Intensity, Counts per Seconds (CPS) |
|---|---|
| 12.1 | 1530 |
| 13.3 | 3174 |
| 13.4 | 1758 |
| 14.5 | 1034 |
| 15.6 | 814 |
| 15.9 | 1249 |
| 16.9 | 710 |
| 18.8 | 700 |
| 19.4 | 1605 |
| 20.8 | 6982 |
| 21.6 | 2193 |
| 22.7 | 1225 |
| 22.8 | 1045 |
| 24.2 | 756 |
| 25.0 | 1809 |
| 26.0 | 705 |
| 29.9 | 833 |
| 30.5 | 994 |
| 34.2 | 1269 |

Infrared (IR) Spectroscopy

IR spectra (e.g., see FIG. 5) were acquired as follows. Samples were prepared as potassium bromide (KBr) discs (or pellets). A small amount of each sample (about 3 mg) was ground in a hard surface mortar until glossy in appearance. One half gram (0.5 g) of KBr was added to the sample and the mixture was continuously ground until well mixed. The mixture was then transferred to a die and pressed into a disc using a hydraulic press.

Figure 5:
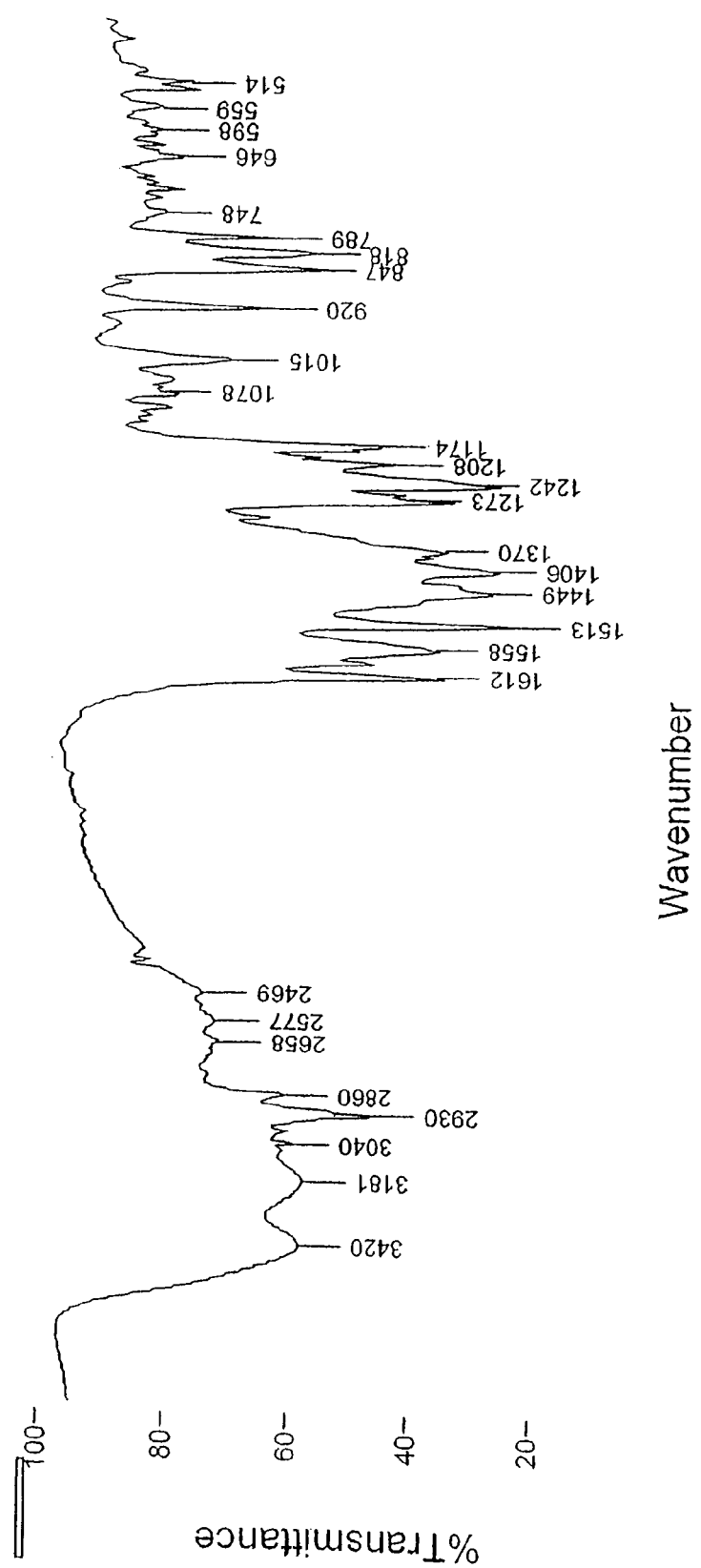
FIG. 5 depicts an IR spectrum of the bazedoxifene acetate Form B polymorph in KBr pellet.

The IR spectrum of FIG. 5 was obtained using a DIGILAB EXCALIBUR Series FTS-4000 FT-IR Spectrometer operated at 4 $cm^{-1}$ resolution and 16 scans between 400-4000 $cm^{-1}$.

Differential Scanning Calorimetry (DSC)

Figure 6:
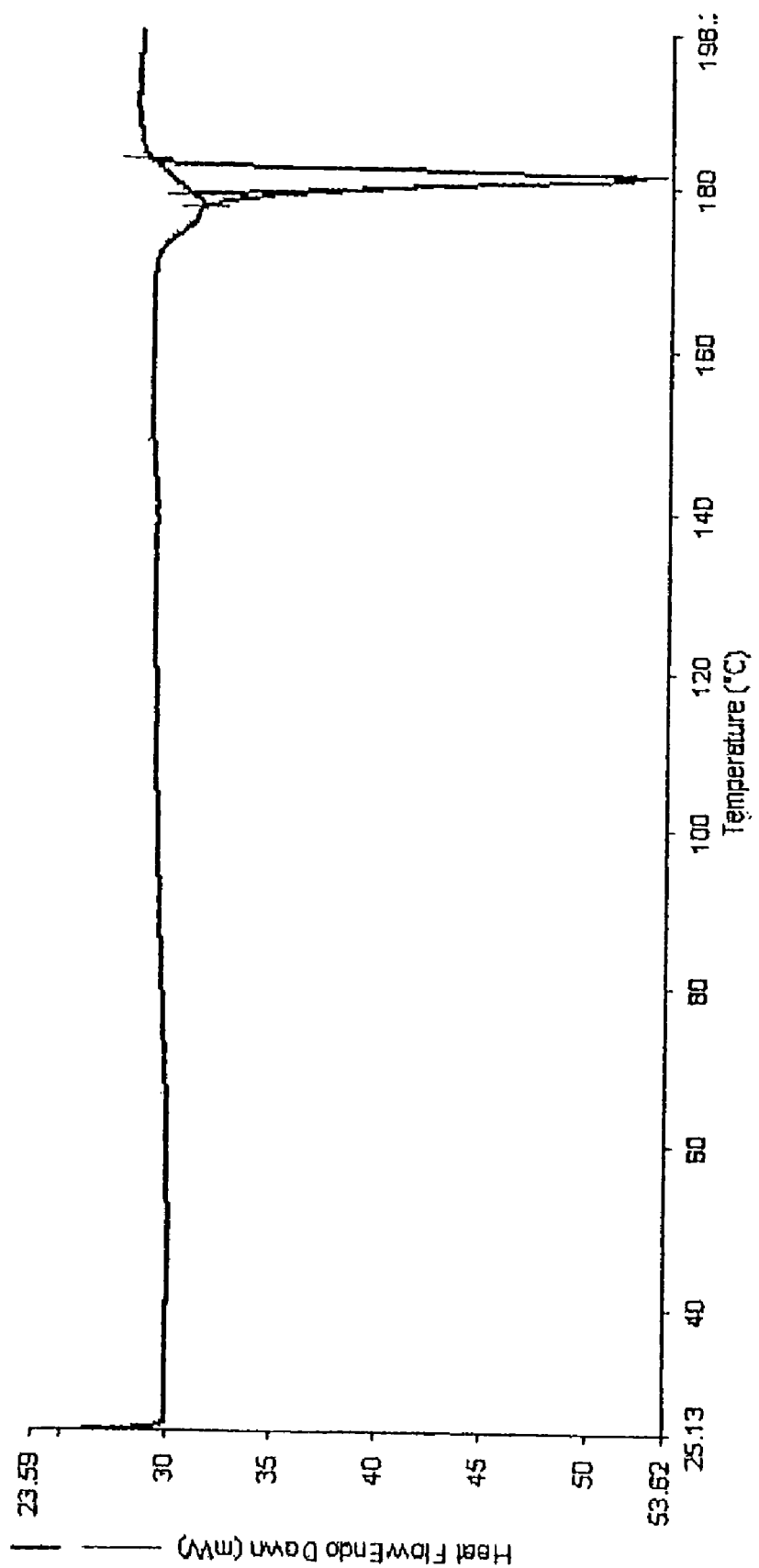
FIG. 6 depicts a differential scanning calorimetry (DSC) trace of bazedoxifene acetate Form B polymorph.

DSC measurements (see FIG. 6) were carried out in both sealed pan and vented pan at a scan rate of 10° C./min from 25° C. to 200° C. under nitrogen purge using a Pyris I DSC from Perkin-Elmer.

EXAMPLE 7

Pharmacokinetic Analysis of A Direct Blend Formulation of the Invention in Dogs

A direct blend tablet formulation in accordance with Example 1, supra, was compared in female Beagle Dogs to a tablet formulation prepared by a wet granulation process.

The composition of the wet granulation formulation is shown in the Table below:

| Ingredient | % WT/WT | mg/tablet |
|---|---|---|
| Bazedoxifene Acetate, micronized | 4.843[a] | 20.00[a] |
| Lactose, NF (fast flow) | 35.206 | 145.40 |
| AVICEL PH101 ® (microcrystalline cellulose) | 33.898 | 140.00 |
| Pregelatinized Starch NF (STARCH 1500 ®) | 13.559 | 56.00 |
| Sodium Lauryl Sulfate NF | 1.453 | 6.00 |
| Sodium Starch Glycolate NF | 5.811 | 24.00 |
| Ascorbic Acid, USP Fine Powder | 1.453 | 6.00 |
| Silicon Dioxide (SYLOID ® 244 FP) | 0.145 | 0.60 |
| Magnesium Stearate NF | 0.484 | 2.00 |
| White OPADRY ® 1 (YS-1-18027-A) | 3.148 | 13.00 |
| Water, USP, Purified | qs | qs |
| TOTAL | 100.00 | 413.0 mg |

[a] As the free base, quantity is adjusted based on actual potency. Corresponding adjustment was made with lactose Each of six female dogs (7.2-11.0 kg), received a single 10 mg dose of bazedoxifene acetate from both formulations following an overnight fast in a non-randomized crossover design. 20 mg wet granulation tablets as described above were broken in half for the 10 mg dose from that formulation. Blood samples were drawn at 0 (predose), 0.5, 1, 2, 3, 4, 6, 8, 12 and 24 hours after dosing, plasma was separated and assayed for bazedoxifene acetate content.

Individual dog plasma bazedoxifene concentration-time profiles were subjected to noncompartmental pharmacokinetic analyses (WinNonlin, Model 200). The following pharmacokinetic parameters were determined for each dog and descriptive statistics were calculated for comparison between the two formulations: $AUC_{0-t}$, $C_{max}$, $t_{max}$. The results are summarized in the following Table:

Pharmacokinetic Parameters of Bazedoxifene Acetate in Female Dogs Following Single Oral Dose Administration of 10 mg as Direct Blend Tablet and Tablet Prepared by Wet Granulation Procedure

| Parameter | Direct Blend Tablet | Wet Granulation Tablet | Individual Dog Ratios |
|---|---|---|---|
| $AUC_{0-t}$ (ng · hr/mL) | 79.3 | 88.2 | 0.90 |
|  | 171 | 149 | 1.14 |
|  | 61.6 | 106 | 0.58 |
|  | 65.4 | 139 | 0.47 |
|  | 112 | 48.0 | 2.33 |
|  | 82.2 | 158 | 0.52 |
| Mean | 95.2 | 115 | 0.99 |
| SD | 41.0 | 42.2 | 0.71 |

-continued

Pharmacokinetic Parameters of Bazedoxifene Acetate in Female Dogs
Following Single Oral Dose Administration of 10 mg as Direct Blend
Tablet and Tablet Prepared by Wet Granulation Procedure

| Parameter | Direct Blend Tablet | Wet Granulation Tablet | Individual Dog Ratios |
|---|---|---|---|
| $C_{max}$ | 20.7 | 26.6 | 0.78 |
| (ng/mL) | 12.3 | 14.5 | 0.85 |
|  | 5.10 | 13.7 | 0.37 |
|  | 6.74 | 20.0 | 0.34 |
|  | 18.7 | 12.9 | 1.45 |
|  | 8.99 | 14.2 | 0.63 |
| Mean | 12.1 | 17.0 | 0.74 |
| SD | 6.42 | 5.36 | 0.41 |
| $t_{max}$ | 1.00 | 0.50 |  |
| (hr) | 4.00 | 1.00 |  |
|  | 2.00 | 0.50 |  |
|  | 4.00 | 1.00 |  |
|  | 0.50 | 0.50 |  |
|  | 0.50 | 1.00 |  |
| Mean | 2.00 | 0.75 |  |
| SD | 1.64 | 0.27 |  |

Because of the variability in the plasma bazedoxifene levels typically observed in this protocol, terminal elimination half-lives could not be determined for the majority of the plasma bazedoxifene concentration-time profiles; therefore $AUC_{0-t}$ values were compared between the two tablet formulations. Also, the exposure levels of bazedoxifene from the direct blend tablet appeared to be slightly lower than those from the wet granulation tablet.

Figure 7:
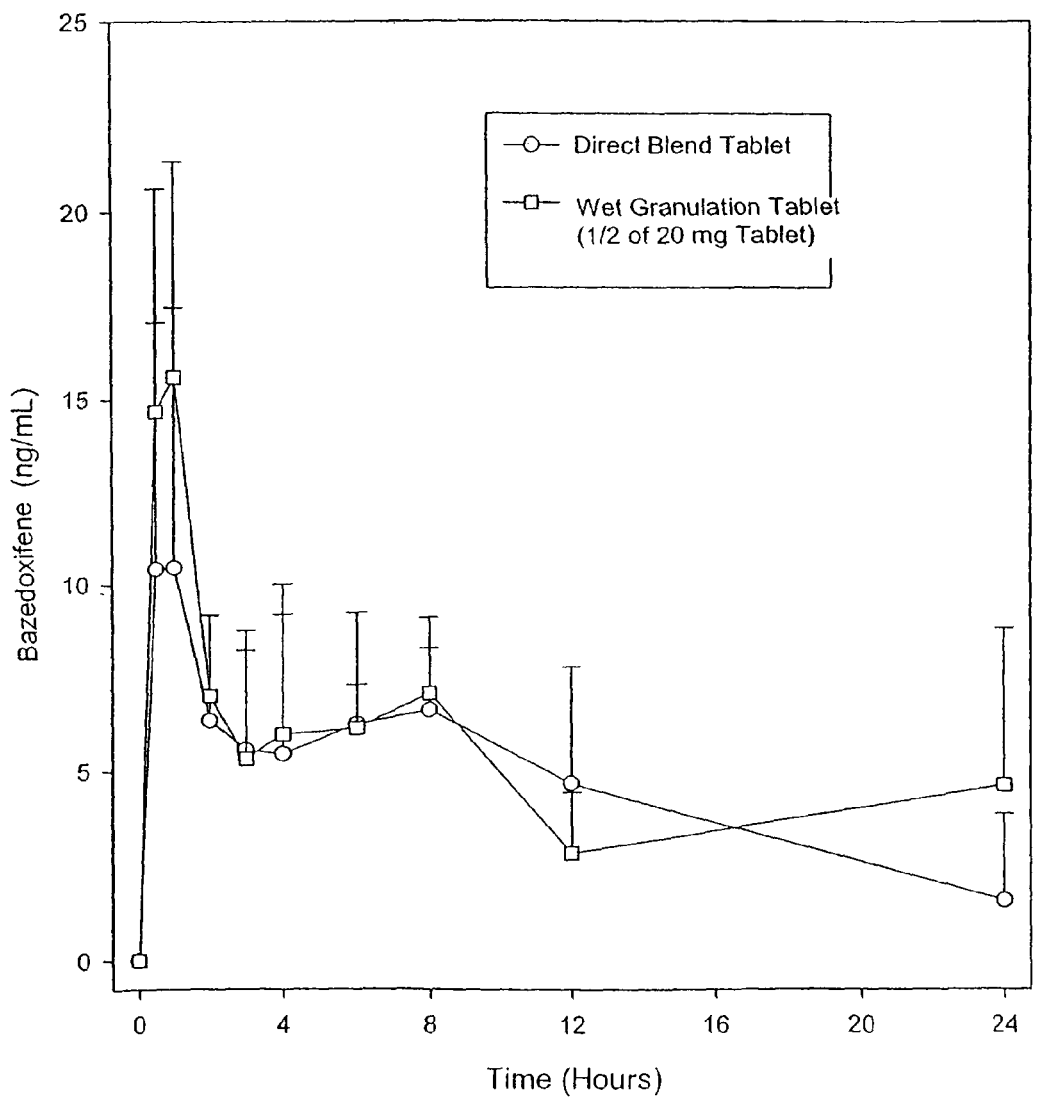
FIG. 7 shows the mean (SD) plasma bazedoxifene levels in female dogs following single oral dose administration of 10 mg bazedoxifene as direct blend tablet, and a wet granulation tablet, as described in Example 7.
Figure 8:
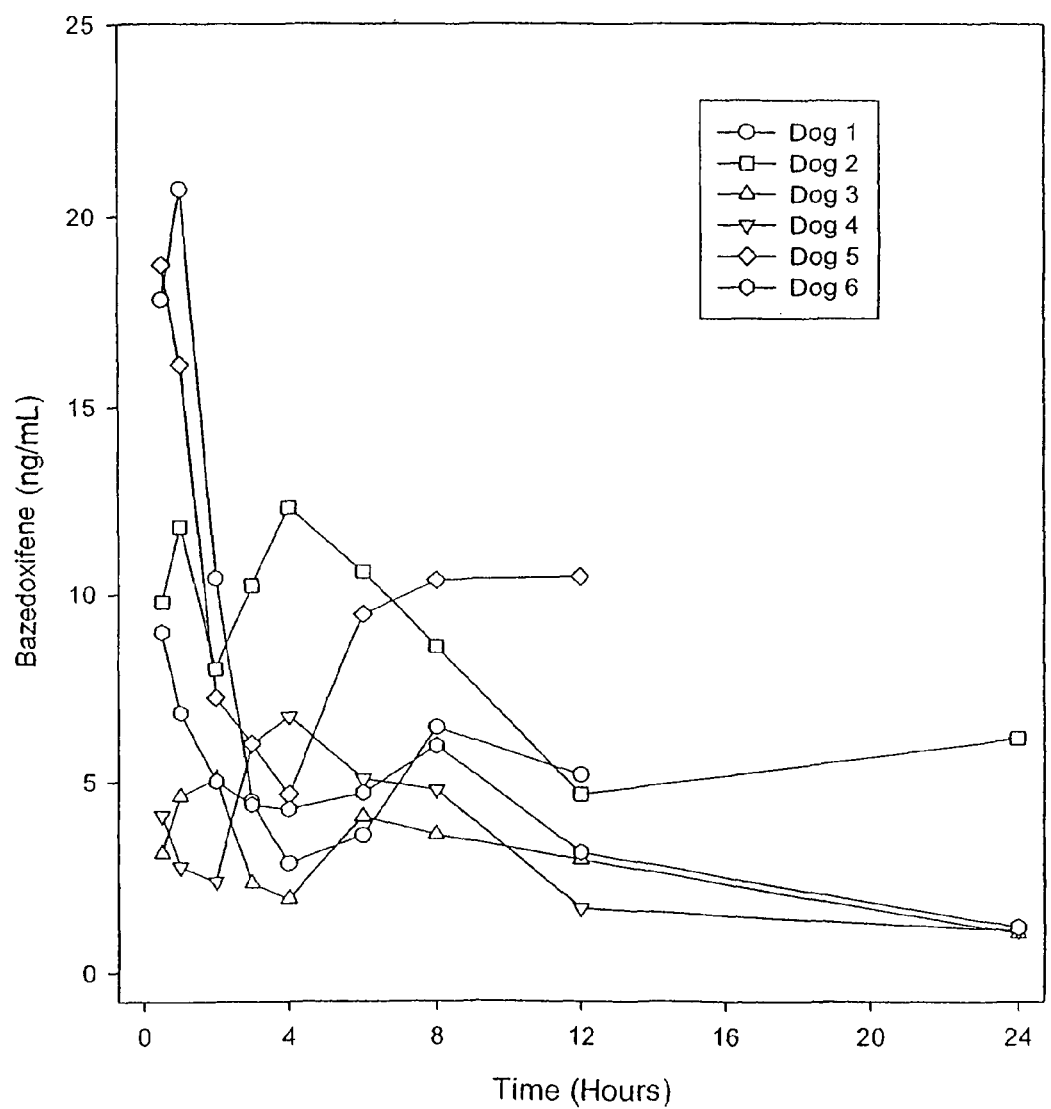
FIG. 8 shows individual dog plasma bazedoxifene levels following single oral dose administration of 10 mg bazedoxifene direct blend tablets.
Figure 9:
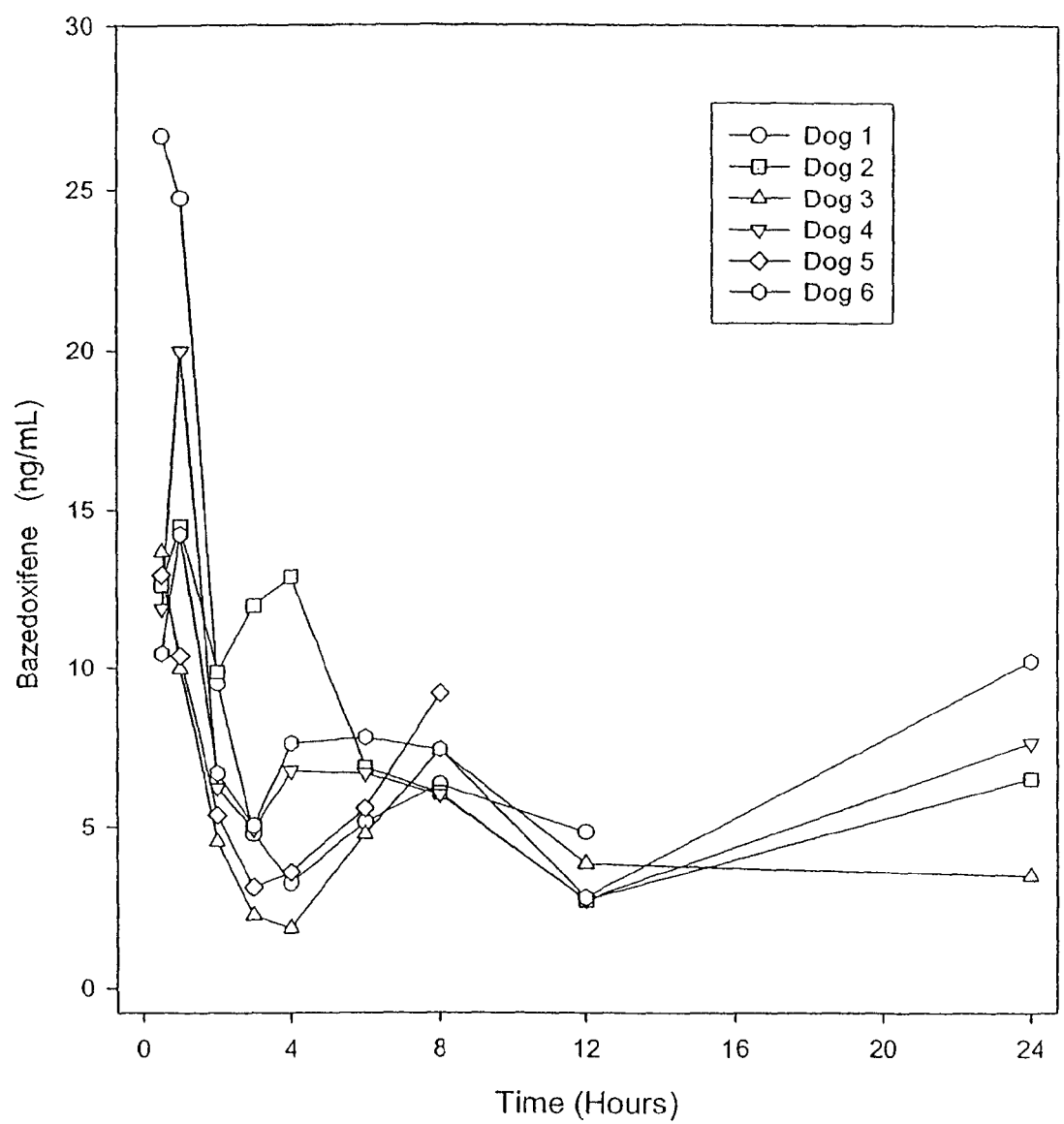
FIG. 9 shows individual dog plasma bazedoxifene levels following single oral dose administration of 10 mg bazedoxifene wet granulated tablets.

FIG. 7 shows the mean (SD) plasma bazedoxifene levels in female dogs following single oral dose administration of 10 mg bazedoxifene as direct blend tablet of Example 1, and the wet granulated tablet described above. FIG. 8 shows individual dog plasma bazedoxifene levels following single oral dose administration of the 10 mg bazedoxifene direct blend tablets, and FIG. 9 shows individual dog plasma bazedoxifene levels following single oral dose administration of 10 mg bazedoxifene via the wet granulated tablet described above.

As can be seen from these data, the direct blend formulation prepared in accordance with the present invention provides administration of bazedoxifene that is comparable to that provided by the tablets prepared by the wet granulation process.

Various modifications of the invention, in addition to those described herein, will be apparent to those skilled in the art from the foregoing description. Such modifications are also intended to fall within the scope of the appended claims. Each of the publications and, references, including books and patents, cited in the present application is incorporated herein by reference in its entirety.

What is claimed is:

1. A pharmaceutical composition comprising:
   a pharmaceutically effective amount of bazedoxifene acetate, wherein at least 80% of said bazedoxifene acetate is present in the A polymorph form, and
   a carrier or excipient system, the carrier or excipient system comprising:
   a) a first filler/diluent component comprising from about 5% to about 85% by weight of the pharmaceutical formulation;
   b) an optional second filler/diluent component comprising from about 5% to about 85% by weight of the pharmaceutical formulation;
   c) an optional antioxidant component comprising up to about 15% by weight of the pharmaceutical formulation;
   d) a glidant/disintegrant component comprising from about 0.01% to about 10% by weight of the pharmaceutical formulation; and
   e) a lubricant component comprising from about 0.01% to about 10% by weight of the pharmaceutical formulation.

2. A pharmaceutical composition of claim 1, wherein said bazedoxifene acetate comprises from about 0.1% to about 30% by weight of the pharmaceutical formulation.

3. A pharmaceutical composition of claim 1, wherein said bazedoxifene acetate comprises from about 10% to about 30% by weight of the pharmaceutical formulation.

4. A pharmaceutical composition of claim 1, wherein said bazedoxifene acetate is present in the A polymorph form.

5. A pharmaceutical composition of claim 1, wherein at least 90% of said bazedoxifene acetate is present in the A polymorph form.

6. A pharmaceutical composition of claim 1, wherein:
   said bazedoxifene acetate comprises from about 10% to about 30% by weight of the pharmaceutical formulation;
   said first filler/diluent component comprising from about 25% to about 50% by weight of the pharmaceutical formulation;
   said optional second filler/diluent component comprising from about 25% to about 50% by weight of the pharmaceutical formulation; said optional antioxidant component comprising from about 1% to about 10% by weight of the pharmaceutical formulation;
   said glidant/disintegrant component comprising from about 1% to about 10% by weight of the pharmaceutical formulation; and
   said lubricant component comprising about 0.01% to about 3% by weight of the pharmaceutical formulation.

7. A pharmaceutical composition of claim 6, wherein:
   said first filler/diluent component comprising from about 25% to about 42% by weight of the pharmaceutical formulation; and
   said optional second filler/diluent component comprising from about 25% to about 42% by weight of the pharmaceutical formulation.

8. A pharmaceutical composition of claim 1, wherein said first filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, and metal aluminosilicates.

9. A pharmaceutical composition of claim 1, wherein the filler/diluent component comprises microcrystalline cellulose.

10. A pharmaceutical composition of claim 1, wherein said optional second filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, and metal aluminosilicates.

11. A pharmaceutical composition of claim 1, wherein said optional second filler/diluent component comprises lactose.

12. A pharmaceutical composition of claim 1, wherein the glidant/disintegrant component comprises one or more components selected from the group consisting of croscarmellose sodium, modified cellulose, pregelatinized starch, sodium starch glycolate, crospovidone, starch, alginic acid, sodium alginate, clays, cellulose floc, ion exchange resins, effervescent systems based on food acids, amorphous fumed silica, talc, lactose, metal stearates, dibasic calcium phosphate, magnesium carbonate, magnesium oxide, calcium silicate, silica, silicon dioxide and silicon dioxide aerogels.

13. A pharmaceutical composition of claim 1, wherein said glidant/disintegrant component comprises sodium starch glycolate.

14. A pharmaceutical composition of claim 1, wherein said lubricant component comprises one or more components selected from the group consisting of metal stearates, fatty acid esters, fatty acids, fatty alcohols, glyceryl behenate, mineral oil, paraffins, hydrogenated vegetable oils, leucine, polyethylene glycols, amorphous fumed silica, and sodium chloride.

15. A pharmaceutical composition of claim 1, wherein said lubricant component comprises magnesium stearate.

16. A pharmaceutical composition of claim 1, wherein said optional antioxidant component comprises one or more of ascorbic acid, sodium ascorbate, ascorbyl palmitate, BHT or BHA.

17. A pharmaceutical composition of claim 1, wherein said optional antioxidant component comprises ascorbic acid.

18. A pharmaceutical composition of claim 1, wherein:
said first filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, or metal aluminosilicates;
said optional second filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, or metal aluminosilicates;
said optional antioxidant component comprises one or more components selected from the group consisting of ascorbic acid, sodium ascorbate or ascorbyl palmitate;
said glidant/disintegrant component comprises one or more components selected from the group consisting of croscarmellose sodium, modified cellulose, pregelatinized starch, sodium starch glycolate, crospovidone, starch, alginic acid, sodium alginate, clays, cellulose floc, ion exchange resins, effervescent systems based on food acids, amorphous fumed silica, talc, lactose, metal stearates, dibasic calcium phosphate, magnesium carbonate, magnesium oxide, calcium silicate, silica, silicon dioxide and silicon dioxide aerogels; and
said lubricant component comprises one or more components selected from the group consisting of metal stearates, fatty acid esters, fatty acids, fatty alcohols, glyceryl behenate, mineral oil, paraffins, hydrogenated vegetable oils, leucine, polyethylene glycols, amorphous fumed silica, and sodium chloride.

19. A pharmaceutical composition of claim 1, wherein:
said first filler/diluent component comprises microcrystalline cellulose;
said optional second filler/diluent component comprises a sugar;
said optional antioxidant component comprises ascorbic acid;
said glidant/disintegrant component comprises sodium starch glycolate; and
said lubricant component comprises a metal stearate.

20. A pharmaceutical composition of claim 1, wherein:
said first filler/diluent component comprises microcrystalline cellulose;
said optional second filler/diluent component comprises lactose NF;
said optional antioxidant component comprises ascorbic acid;
said glidant/disintegrant component comprises sodium starch glycolate; and
said lubricant component comprises magnesium stearate.

21. A pharmaceutical composition of claim 7, wherein:
said first filler/diluent component comprises microcrystalline cellulose;
said optional second filler/diluent component comprises lactose NF;
said optional antioxidant component comprises ascorbic acid;
said glidant/disintegrant component comprises sodium starch glycolate; and
said lubricant component comprises magnesium stearate.

22. A pharmaceutical composition of claim 1, wherein the composition contains from about 0.1 mg to about 300 mg of said bazedoxifene acetate.

23. A pharmaceutical composition of claim 1, wherein the composition contains from about 0.5 mg to about 230 mg of said bazedoxifene acetate.

24. A pharmaceutical composition of claim 1, wherein the composition contains from about 1 mg to about 170 mg of said bazedoxifene acetate.

25. A pharmaceutical composition of claim 1, wherein the composition contains from about 5 mg to about 115 mg of said bazedoxifene acetate.

26. A pharmaceutical composition of claim 1, wherein the composition contains from about 1 mg to about 30 mg of said bazedoxifene acetate.

27. A tablet comprising a pharmaceutical composition of claim 1.

28. A tablet comprising a pharmaceutical composition of claim 3.

29. A tablet comprising a pharmaceutical composition of claim 18.

30. A tablet comprising a pharmaceutical composition of claim 21.

31. A tablet of claim 27 further comprising one or more coatings.

32. A pharmaceutical composition of claim 1 wherein said composition is prepared by a non-aqueous process.

33. A pharmaceutical composition of claim 32 wherein said non-aqueous process is direct blending.

34. A pharmaceutical composition of claim 32 wherein said non-aqueous process is dry granulation.

35. A pharmaceutical composition of claim 32 wherein said non-aqueous process is roller compaction.

36. A tablet comprising a composition according to any of claims 32-35.

37. A capsule containing a composition according to any of claims 32-35.

38. The pharmaceutical composition of claim 1, wherein the pharmaceutical composition is prepared by a non-aqueous process comprising direct blending, dry granulation, or roller compaction.

39. The pharmaceutical composition of claim 38, wherein the non-aqueous process is a direct blend process comprising:
  i) combining the bazedoxifene acetate, first filler/diluent, second filler/diluent, glidant, and, optionally, the antioxidant to form a first mixture;
  ii) blending the first mixture to form a blended first mixture;
  iii) adding the lubricant to the blended first mixture to form a second mixture; and
  iv) optionally blending the second mixture to form a blended second mixture; and
  v) optionally,
    compressing at least a portion of the second mixture, or the blended second mixture, to form a tablet therefrom; or
    filling a capsule with the second mixture, or the blended second mixture, to provide a capsule filled with the second mixture, or the blended second mixture.

40. The pharmaceutical composition of claim 38, wherein at least 90% of the bazedoxifene acetate is present in the A polymorph form.

41. The pharmaceutical composition of claim 39, wherein at least 90% of the bazedoxifene acetate is present in the A polymorph form.

42. The pharmaceutical composition of claim 39, wherein:
  the first filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, or metal aluminosilicates;
  the optional second filler/diluent component comprises one or more components selected from the group consisting of sugars, mannitol, lactose, sucrose, powdered cellulose, microcrystalline cellulose, malodextrin, sorbitol, starch, xylitol, carboxymethyl cellulose, carboxyethyl cellulose, hydroxyethyl celluloses, microcrystalline celluloses, starches, anhydrous dicalcium phosphate, sodium starch glycolates, or metal aluminosilicates;
  the optional antioxidant component comprises one or more components selected from the group consisting of ascorbic acid, sodium ascorbate or ascorbyl palmitate;
  the glidant/disintegrant component comprises one or more components selected from the group consisting of croscarmellose sodium, modified cellulose, pregelatinized starch, sodium starch glycolate, crospovidone, starch, alginic acid, sodium alginate, clays, cellulose floc, ion exchange resins, effervescent systems based on food acids, amorphous fumed silica, talc, lactose, metal stearates, dibasic calcium phosphate, magnesium carbonate, magnesium oxide, calcium silicate, silica, silicon dioxide and silicon dioxide aerogels; and
  the lubricant component comprises one or more components selected from the group consisting of metal stearates, fatty acid esters, fatty acids, fatty alcohols, glyceryl behenate, mineral oil, paraffins, hydrogenated vegetable oils, leucine, polyethylene glycols, amorphous fumed silica, and sodium chloride.

43. The pharmaceutical composition of claim 38, wherein:
  the first filler/diluent component comprises microcrystalline cellulose;
  the optional second filler/diluent component comprises lactose;
  the optional antioxidant component comprises ascorbic acid;
  the glidant/disintegrant component comprises sodium starch glycolate; and
  the lubricant component comprises a metallic stearate.

44. The pharmaceutical composition of claim 38, wherein:
  the first filler/diluent component comprises microcrystalline cellulose;
  the optional second filler/diluent component comprises lactose NF;
  the optional antioxidant component comprises ascorbic acid;
  the glidant/disintegrant component comprises sodium starch glycolate; and
  the lubricant component comprises magnesium stearate.

45. The pharmaceutical composition of claim 39, wherein:
  the first filler/diluent component comprises microcrystalline cellulose;
  the optional second filler/diluent component comprises lactose NF;
  the optional antioxidant component comprises ascorbic acid;
  the glidant/disintegrant component comprises sodium starch glycolate; and
  the lubricant component comprises magnesium stearate.

46. The pharmaceutical composition of claim 38, wherein the pharmaceutical composition contains from about 0.1 mg to about 300 mg of the bazedoxifene acetate.

47. The pharmaceutical composition of claim 39, wherein the pharmaceutical composition contains from about 0.1 mg to about 300 mg of the bazedoxifene acetate.

* * * * *